(12) United States Patent
Akita et al.

(10) Patent No.: US 8,057,039 B2
(45) Date of Patent: Nov. 15, 2011

(54) FUNDUS IMAGING APPARATUS

(75) Inventors: Junichi Akita, Aichi (JP); Akitoshi Yoshida, Asahikawa (JP); Satoshi Ishiko, Asahikawa (JP)

(73) Assignee: Nidek Co., Ltd., Gamagori-Shi (JP)

( * ) Notice: Subject to any disclaimer, the term of this patent is extended or adjusted under 35 U.S.C. 154(b) by 342 days.

(21) Appl. No.: 12/232,879

(22) Filed: Sep. 25, 2008

(65) Prior Publication Data

US 2009/0086164 A1    Apr. 2, 2009

(30) Foreign Application Priority Data

Sep. 29, 2007  (JP) ................................. 2007-256936
Nov. 16, 2007  (JP) ................................. 2007-298568

(51) Int. Cl.
*A61B 3/14* (2006.01)
(52) U.S. Cl. ........................................ 351/206; 351/205
(58) Field of Classification Search .................. 351/205, 351/206, 246, 200
See application file for complete search history.

(56) References Cited

U.S. PATENT DOCUMENTS

| | | | |
|---|---|---|---|
| 6,224,212 B1 | 5/2001 | Noda et al. | |
| 6,404,545 B1 | 6/2002 | Ishiwata | |
| 2002/0060298 A1 | 5/2002 | Endo et al. | |
| 2004/0051847 A1* | 3/2004 | Vilser | 351/200 |

FOREIGN PATENT DOCUMENTS

| | | |
|---|---|---|
| JP | A2000-126134 | 5/2000 |
| JP | A2007-89828 | 4/2007 |
| WO | WO 2006/076772 A1 | 7/2006 |

* cited by examiner

*Primary Examiner* — James Greece
(74) *Attorney, Agent, or Firm* — Oliff & Berridge, PLC

(57) ABSTRACT

A fundus imaging apparatus comprises: an irradiation optical system comprising a light source which emits a laser beam and a scanner which two-dimensionally scans the laser beam on a fundus of an examinee's eye, the irradiation optical system being adapted to focus the laser beam emitted from the light source on the fundus to form a confocal region; an imaging optical system comprising a photo-receiving element which receives reflection light of the laser beam reflected from the fundus, the imaging optical system being adapted to focus the reflection light from the fundus and receive the reflection light by the photo-receiving element; and a beam restriction member placed in an optical path of the imaging optical system, the beam restriction member comprising: one of an opening through which part of the reflection light from the fundus outside the confocal region is allowed to pass toward the photo-receiving element and a mirror part which reflects the part of the reflection light from the fundus outside the confocal region toward the photo-receiving element; and a light shielding part which shields the reflection light from the fundus in the confocal region and the part of the reflection light from the fundus outside the confocal region. The light shielding part includes a first light shielding part placed in a conjugate position with a focus point of the laser beam on the fundus and a second light shielding part placed in a nearly conjugate position with the fundus and adapted to shield part of an optical path of the reflection light, the second light shielding part is formed around the first light shielding part.

12 Claims, 9 Drawing Sheets

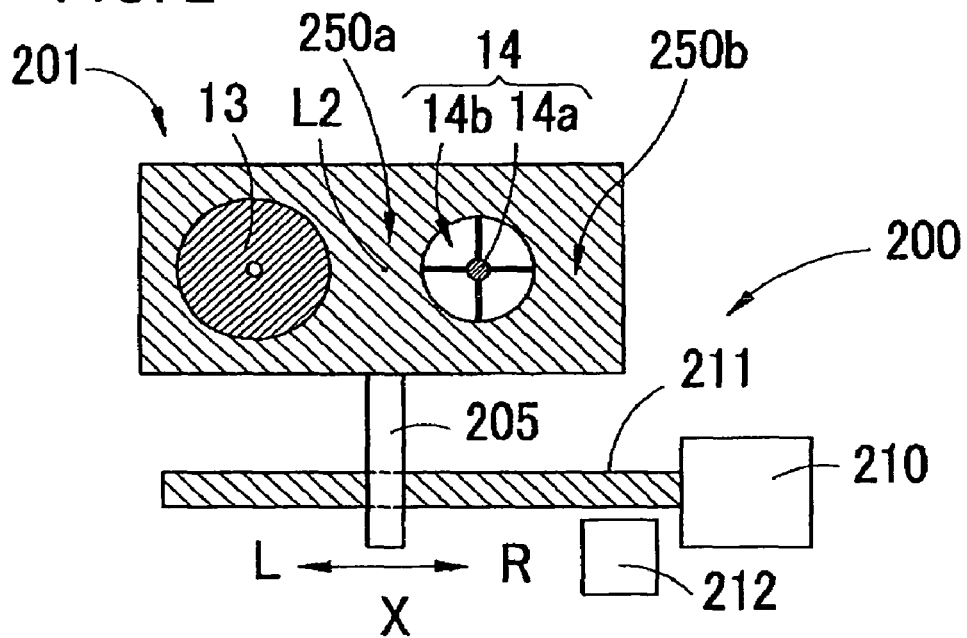
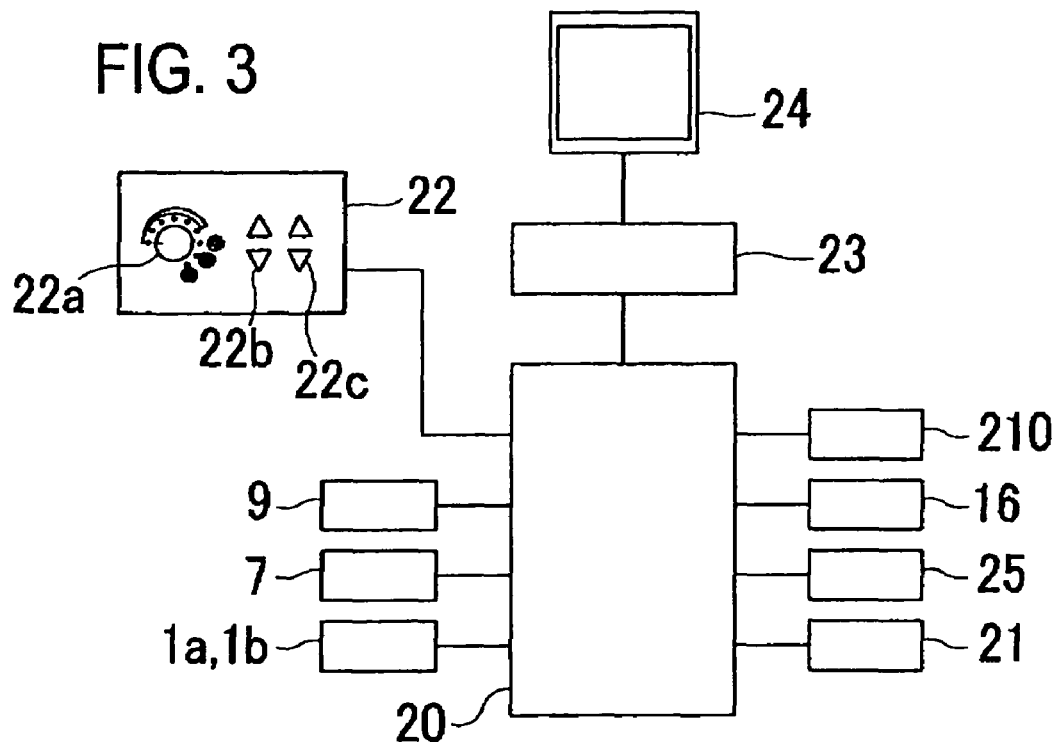

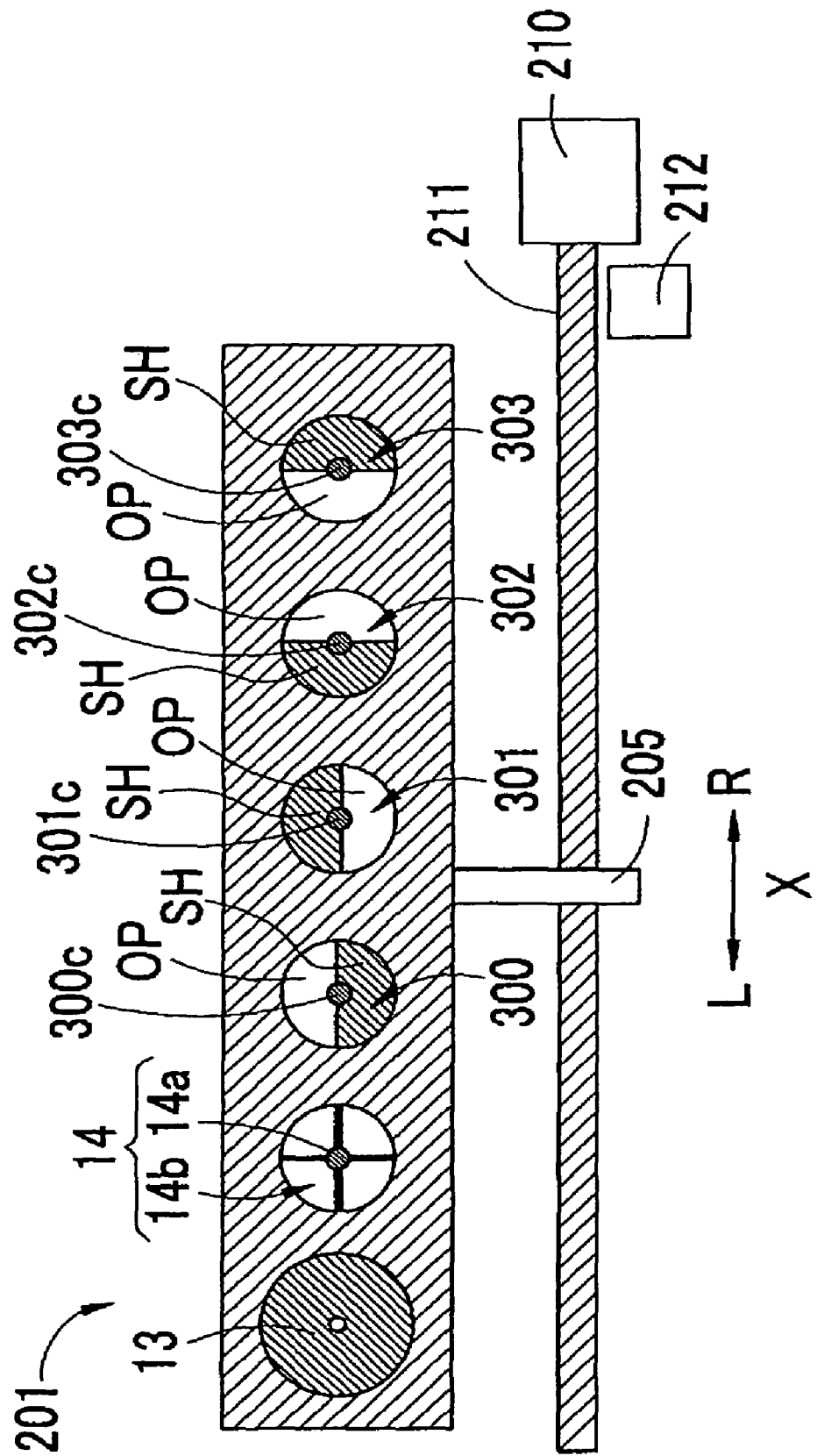

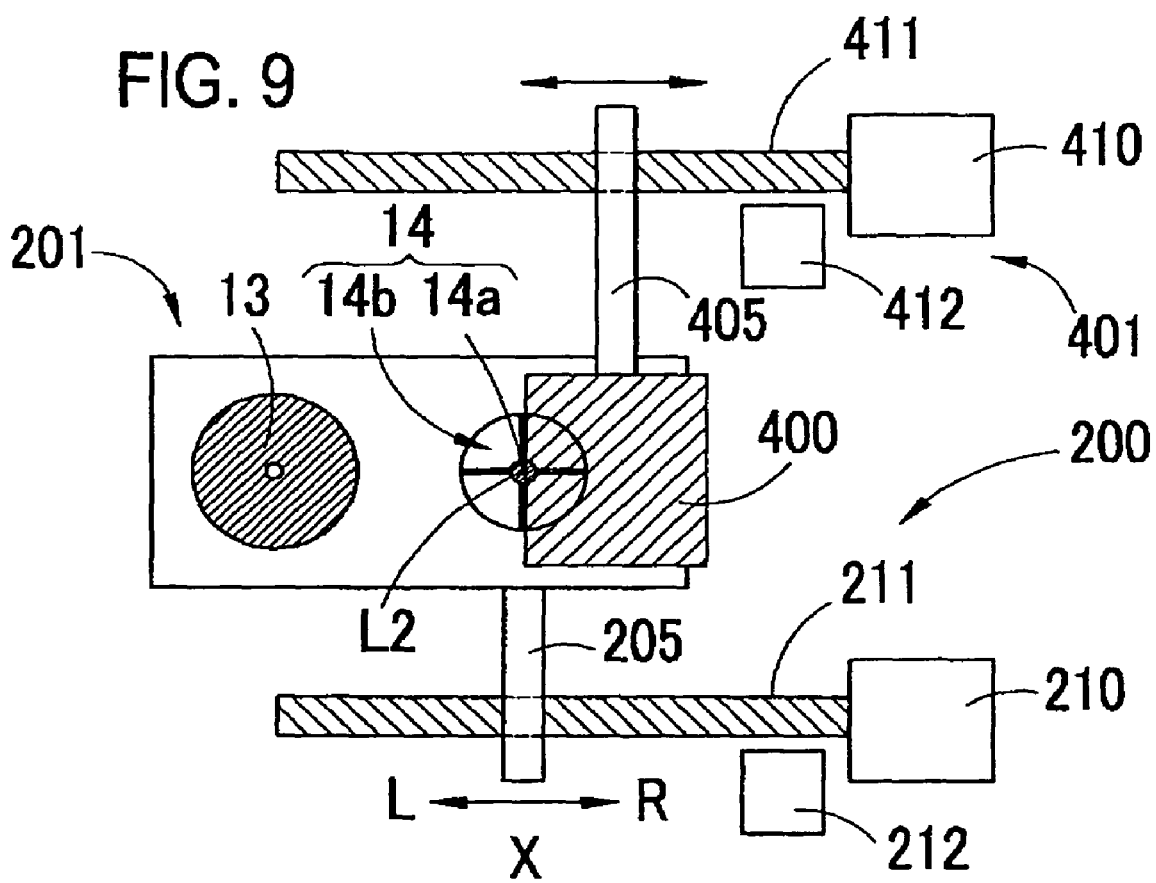

FUNDUS IMAGING APPARATUS

BACKGROUND OF THE INVENTION

1. Field of the Invention

The present invention relates to a fundus imaging apparatus for imaging a fundus of an examinee's eye to observe the fundus.

2. Description of Related Art

There is a known fundus imaging apparatus arranged to two-dimensionally scan a laser beam across a fundus, and receive reflection light therefrom to produce a fundus image. For such fundus imaging apparatus, a technique (Scattered Light Imaging) has been known in which a ring aperture including a ring-shaped opening and a black-spot plate is placed in conjugate relation with a fundus of an examinee's eye to restrict reflection light from a light condensing point (a focus point) on a portion under observation, the method including receiving scattered light from front and back of the light condensing point to create an image (see JP2007-89828A).

In the case of conventional scattered light imaging, meanwhile, scattered light coming from front and back of the light condensing point is extracted through a ring-shaped opening and the scattered light (excluding the light shielded by a black-spot plate) scattered in nearly cone shape in all directions is received by a photo-receiving element. A scattered state of the scattered light is too strong to obscure fine biological materials (e.g. a fiber layer between cells in a fundus) existing on the fundus. It is therefore difficult to image such fine biological materials in an observable state.

BRIEF SUMMARY OF THE INVENTION

The present invention has been made in view of the above circumstances and has an object to provide a fundus imaging apparatus capable of obtaining a fundus image useful in diagnosis of a fundus of an examinee's eye.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a fundus imaging apparatus comprising: an irradiation optical system comprising a light source which emits a laser beam and a scanner which two-dimensionally scans the laser beam on a fundus of an examinee's eye, the irradiation optical system being adapted to focus the laser beam emitted from the light source on the fundus to form a confocal region; an imaging optical system comprising a photo-receiving element which receives reflection light of the laser beam reflected from the fundus, the imaging optical system being adapted to focus the reflection light from the fundus and receive the reflection light by the photo-receiving element; and a beam restriction member placed in an optical path of the imaging optical system, the beam restriction member comprising: one of an opening through which part of the reflection light from the fundus outside the confocal region is allowed to pass toward the photo-receiving element and a mirror part which reflects the part of the reflection light from the fundus outside the confocal region toward the photo-receiving element; and a light shielding part which shields the reflection light from the fundus in the confocal region and the part of the reflection light from the fundus outside the confocal region, wherein the light shielding part includes a first light shielding part placed in a conjugate position with a focus point of the laser beam on the fundus and a second light shielding part placed in a nearly conjugate position with the fundus and adapted to shield part of an optical path of the reflection light, the second light shielding part is formed around the first light shielding part.

According to the invention, a fundus image useful in diagnosis of a fundus of an examinee's eye can be obtained.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 2 is a diagram to explain a concrete configuration of a movement mechanism;

FIG. 3 is a block diagram showing a control system of the fundus imaging apparatus in the embodiment;

FIG. 8 is a diagram showing an example in which a plurality of light shielding members is provided, each having an opening that allows part of scattered light to pass therethrough toward a photo-receiving element;

FIG. 9 is an explanatory view of a second embodiment; and

DETAILED DESCRIPTION OF THE PREFERRED EMBODIMENTS

Figure 1:
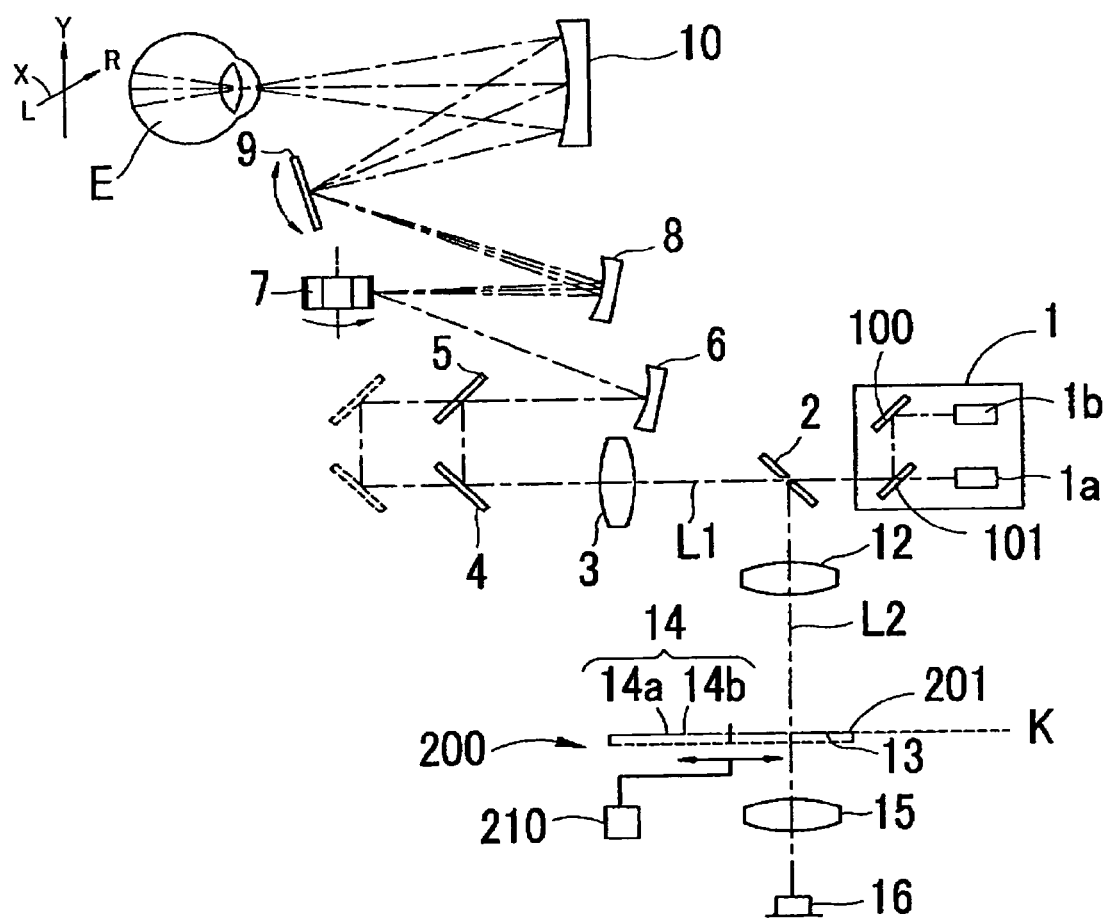
FIG. 1 is a diagram showing an optical system of a fundus imaging apparatus in an embodiment.

A detailed description of a preferred embodiment of the present invention will now be given referring to the accompanying drawings. FIG. 1 is a diagram showing an optical system of a fundus imaging apparatus in this embodiment. In the following explanation, an X-direction represents right and left direction and a Y-direction represents up and down direction. The right (R) direction indicates a right-hand direction of the apparatus when an examinee is seen from the apparatus facing the examinee and the left (L) direction indicates a left-hand direction of the apparatus when the examinee is seen from the apparatus facing the examinee.

Numeral 1 is a laser beam emission part capable of emitting a laser beam of a first wavelength and a laser beam of a second wavelength. This emission part 1 includes a first laser source 1a that emits a laser beam having a wavelength in an infrared region, a second laser source 1b that emits a laser beam having a wavelength in a visible range, a mirror 100, and a dichroic mirror 101. In this embodiment, the first laser source 1a is arranged to emit a laser beam having a wavelength around 790 nm and the second laser source 1b is arranged to emit a laser beam having a wavelength around 490 nm. The infrared laser beam emitted from the first laser source 1a passes through the dichroic mirror 101 and goes out of the emission part 1 to travel along an optical axis L1. The visible laser beam emitted from the second laser source 1b is deflected by the mirror 100 and then reflected by the dichroic mirror 101 to go out of the emission part 1 and travel along the optical axis L1.

Numeral 2 is a perforated mirror having an opening in the center, 3 is a lens, 4 and 5 are mirrors movable in an arrow direction in FIG. 1, whereby changing the length of an optical path for making focus adjustment (diopter correction), and 6, 8, and 10 are concave mirrors. Numeral 7 is a polygon mirror serving as a deflector for deflecting and scanning a laser beam horizontally on a fundus of an examinee's eye (hereinafter, simply referred to as "fundus"). Numeral 9 is a galvano mirror serving as a deflector for deflecting and scanning a laser beam in a direction perpendicular to the scanning direction by the polygon mirror 7.

The laser beam emitted from the emission part 1 passes through the opening of the perforated mirror 2 and the lens 3 and then is reflected by the mirrors 4 and 5 and the concave mirror 6 toward the polygon mirror 7. The laser beam reflected by the polygon mirror 7 is reflected by the concave mirror 8, the galvano mirror 9, and the concave mirror 10 in turn to focus on an observation surface of the fundus, and scan the fundus in two dimensions (in the X and Y directions in the figure). The above optical components constitute an irradiation optical system including an optical member for focusing a laser beam on the observation surface of the fundus and a scanning means for two-dimensionally scanning the laser beam on the fundus.

Numeral 12 is a lens, 13 is a variable diaphragm whose opening is changeable in diameter, and 14 is a ring aperture having a black-spot plate 14a and a ring-shaped opening 14b. The variable diaphragm 13 and the ring aperture 14 are selectively placed in the optical axis L by a movement mechanism 200. By the lens 12, the variable diaphragm 13 (the ring aperture 14) placed on the optical axis L is conjugated with an observation point on the fundus. Numeral 15 is a focus lens and 16 is a photo-receiving element. This photo-receiving element 16 used in this embodiment is an Avalanche Photodiode (APD).

Reflection light of the laser beam scanned on the fundus travels back along the aforementioned irradiation optical system and is reflected downward by the perforated mirror 2. A position of a pupil of the examinee's eye and the opening of the perforated mirror 2 are conjugated 15 with each other by the lens 3. Reflection light reflected by the perforated mirror 2 is focused (once condensed) on the opening of the variable diaphragm 13 through the lens 2. Reflection light focused on the opening passes through the lens 15 and then enters the photo-receiving element 16. Those optical components constitute an imaging optical system which shares at least part of the irradiation optical system. The imaging optical system is arranged to once condense the reflection light of the laser beam reflected by the fundus and then receive the light by the photo-receiving element to obtain an imaged image. Furthermore, a confocal optical system is constituted by the optical components of the irradiation optical system and the imaging optical system.

The movement mechanism 200 is a mechanism for moving the beam restriction member (a movable member 201) located in a conjugate position in the optical path of the imaging optical system with respect to the fundus. The beam restriction member placed in the optical path of the imaging optical system is positioned outside a common optical path of the imaging optical system and the irradiation optical system. In FIG. 1, the movable member 201 is illustrated to be movable front and back for convenience, but it is actually movable in the X direction (in the right and left direction).

FIG. 2 is a diagram to explain a concrete configuration of the movement mechanism 200 when viewed from the lens 12 side. In FIG. 2, the movement mechanism 200 is arranged to move the movable member 201 on a plane (in the right and left direction) orthogonally intersecting with an optical axis L2 of the imaging optical system. This movement mechanism 200 includes a drive part 210 (e.g. a pulse motor) serving as a drive source for moving the movable member 201, a screw rod 211 coupled with a rotation shaft of the drive part 210, and a connection member 205 formed with a female screw part which engages with a male screw part of the screw rod 211 and connected to the movable member 201.

On the movable member 201, the variable diaphragm 13 and the ring aperture 14 are arranged side by side in a direction perpendicular to the imaging optical axis L2. A portion between an outer edge of the ring aperture 14 and an outer edge of the movable member 201 is used as light shielding parts 250a and 250b. In this case, the light shielding part 250a is positioned on the right of the ring aperture 14 on the drawing sheet (FIG. 1) and the light shielding part 250b is positioned on the left of the ring aperture 14 on the drawing sheet (FIG. 1).

Herein, when the drive part 210 is activated, the screw rod 211 is rotated, moving the movable member 201 in the right and left direction through the connection member 205, thereby selectively placing the variable diaphragm 13 and the ring aperture 14 onto the optical path of the imaging optical system. The movement mechanism 200 is provided with a reference position sensor 212 (e.g. a photo sensor) for detecting a position used as a reference for moving the movable member 201. Accordingly, for moving the movable member 201 to a predetermined position, a drive signal corresponding to a predetermined movement position previously stored in a memory 25 (see FIG. 3) with respect to a detected position by the sensor 212 as a reference position has only to be supplied to the drive part 210. If the drive part 210 is a pulse motor, a signal having a predetermined pulse number will be supplied to the drive part 210.

The movement position of the movable member 201 in this embodiment is selectable from four patterns stored in the memory 25; i.e., a first position (for confocal imaging) in which the center of the opening of the variable diaphragm 13 is positioned on the optical axis L2, a second position (for all-direction scattered light imaging) in which the ring center (the black-spot plate 14a) of the ring aperture 14 is positioned on the optical axis L2, a third position (for right-region scattered light imaging) in which the light shielding part 250a existing on the left of the ring aperture 14 on the drawing sheet (FIG. 2) is positioned on the optical axis L2, and a fourth position (for left-region scattered light imaging) in which the light shielding part 250b existing on the right of the ring aperture 14 on the drawing sheet (FIG. 2) is positioned on the optical axis L2. The third position and the fourth position are determined so that, in a fundus conjugate plane K, a light shielding region which shields reflection light of the laser beam and a passage region (a transmission region) that passes (transmits) the reflection light in the third position are symmetric with those in the fourth position with respect to the optical axis L2.

FIG. 3 is a block diagram showing a control system of the fundus maging apparatus in this embodiment. Numeral 20 is a controller for controlling the entire apparatus. The controller 20 is connected to the semiconductor laser sources 1a and 1b, the polygon mirror 7, the galvano mirror 9, the photo-detecting element 16, a drive unit 21 for moving the mirrors 4 and 5, a control unit 22 for setting various conditions of the fundus imaging apparatus, an image processing part 23 for creating an image of the fundus based on a signal received by the photo-receiving element 16, the drive part 210, the reference position sensor 212, etc. Numeral 24 is a monitor for displaying the fundus image created by the image processing part 23. Numeral 25 is a memory for storing various information.

The control unit 22 is provided with a dial 22a for adjustment of the opening diameter of the variable diaphragm 13 and adjustment of the passage region by movement of the movable member 201, selection switches 22b for selection of a laser beam, input switches 22c for entering a value of refractive power of the examinee's eye, and others. By turning the dial 22a, the opening diameter of the variable diaphragm 13 is changed stepwise from a small one to a large one. When the dial 22a is further turned from the position to provide the maximum opening diameter of the variable diaphragm 13, the light shielding member placed on the optical axis L2 in FIG. 1 is switched from the diaphragm 13 to the ring aperture 14 (moved from the first position to the second position). When the dial 22a is further turned, thereafter, the movable member 201 is moved to the third position. Subsequently, further turning of the dial 22a causes the movable member 201 to be moved to the fourth position.

Operations of the fundus imaging apparatus having the above configuration will be explained below. An examiner measures examinee's refractive power in advance by use of a refractive power measurement device or the like and enters a measured value of the examinee's refractive power with the switches 22c on the control unit 22. The examiner further selects the movement position of the movable member 201 or a laser beam to be used as illumination light with the dial 22a and the selection switches 22b on the control unit 22. In this case, when the examiner turns the dial 22a, the controller 20 drives and controls the drive part 210 according to the conditions set with the dial 22a and also causes the monitor 24 to display a graphic representing the passage region and the light shielding region of fundus reflection light (scattered light).

Furthermore, the controller 20 drives the drive unit 21 based on the entered refractive power data to move the mirrors 4 and 5 for making diopter correction. After the diopter correction, the examiner operates the apparatus with a joystick or the like not shown to irradiate the laser beam to the fundus of the examinee's eye and makes alignment so that a desired image appears on the monitor 24. In this case, the image processing part 23 creates an imaged image based on a light reception signal obtained by the photo-receiving element 16 and the positions of the polygon mirror 7 and the galvano mirror 9 during operation, and a fundus image of the examinee's eye is displayed on the monitor 24.

Figure 4:
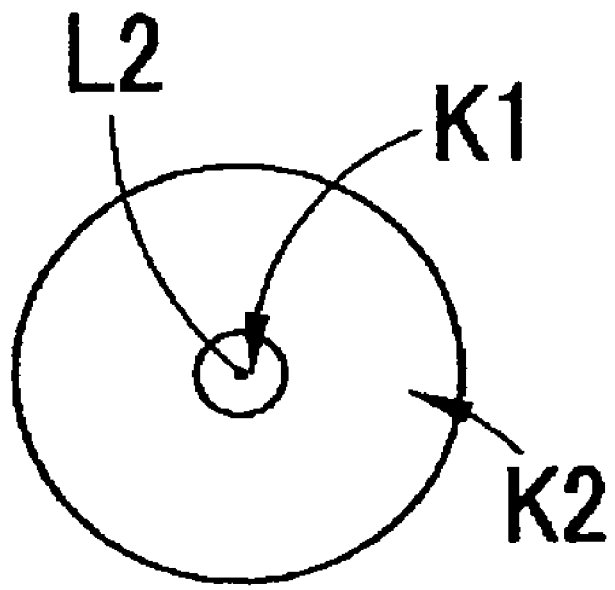
FIG. 4 is a diagram to explain optical paths passing through a fundus conjugate plane.

FIG. 4 is a diagram to explain optical paths passing through the fundus conjugate plane K. FIGS. 5A to 5D are diagrams each showing a passage region and a light shielding region of the light passing through the fundus conjugate plane K when the movable member 201 is moved to the first to fourth positions set in advance, respectively. It should be noted that FIGS. 4 and 5A to 5D show the fundus conjugate plane K formed in the imaging optical system, viewed from the lens 12 side. In FIG. 4, the optical path of the light passing through the fundus conjugate plane K includes a confocal optical path K1 and a scattered light optical path K2. The confocal optical path K1 is formed in a circular shape around the optical axis L2 of the imaging optical system, along which reflection light from a focus point (a light condensing position) on the observation plane mainly passes. The scattered light optical path K2 is formed in a ring shape centered on the optical axis L2 of the imaging optical system, along which scattered light (reflection light) from front and back of the focus point mainly passes.

Figure 5A:
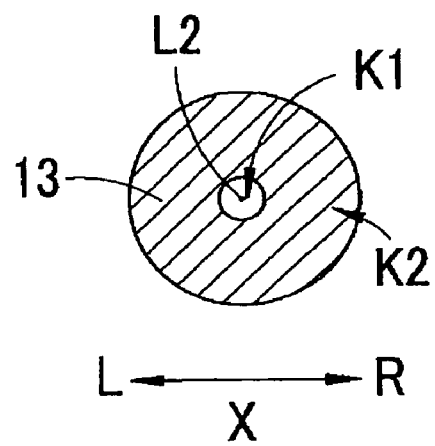
FIGS. 5A to 5D are diagrams showing shielded states of light in passing through the fundus conjugate plane when a movable member is moved by the movement mechanism to previously set, first to fourth positions respectively.

In the case where the movable member 201 is placed in the first position, the variable diaphragm 13 forms the passage region (a white blank portion in the figure) in the confocal optical path K1 and a light shielding region (a hatched portion in the figure) in the scattered light optical path K2, as shown in FIG. 5A. Accordingly, the light reflected from the focus point of the laser beam passes through the opening of the variable diaphragm 13 and enters the photo-receiving element 16, while the scattered light from front and back of the focus point of the laser beam is shielded by the light shielding area formed around the opening of the variable diaphragm 13, so that the passage of scattered light toward the photo-receiving element 16 is restricted. In other words, the variable diaphragm 13 is used as a confocal diaphragm having an opening in a conjugate position with the focus point on the observation plane of the fundus.

Figure 5B:
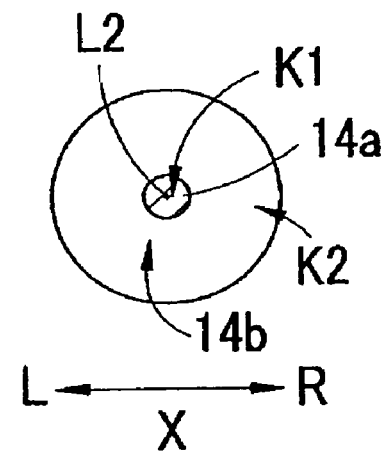
Figure 6A:
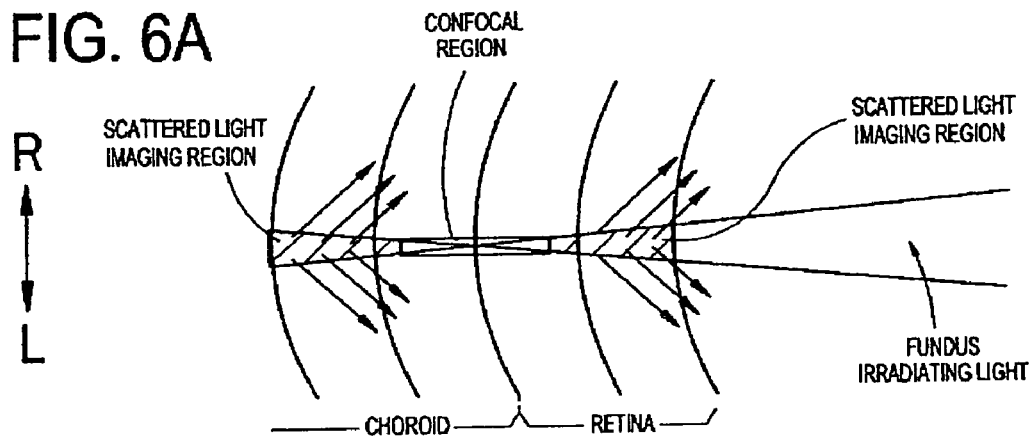
FIGS. 6A to 6C are diagrams to explain shielded states of a laser beam reflected/scattered by a fundus of an examinee's eye.
Figure 6B:
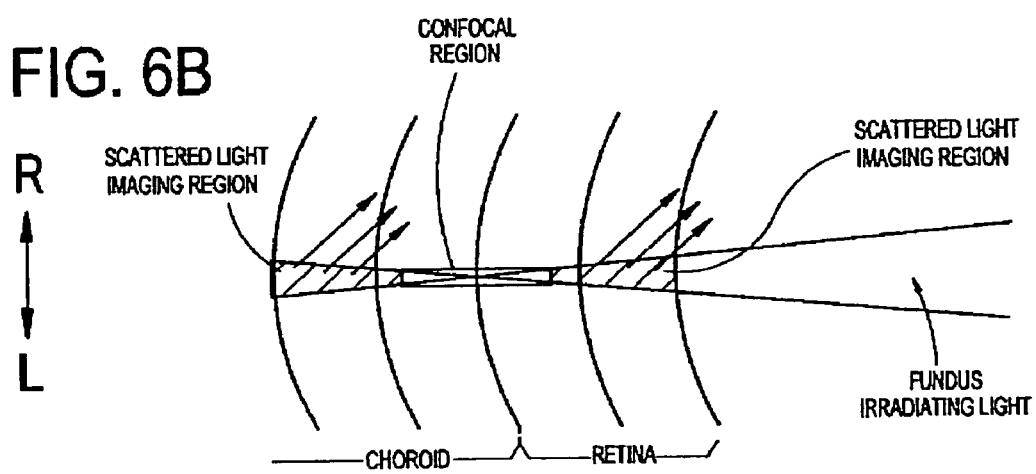
Figure 6C:
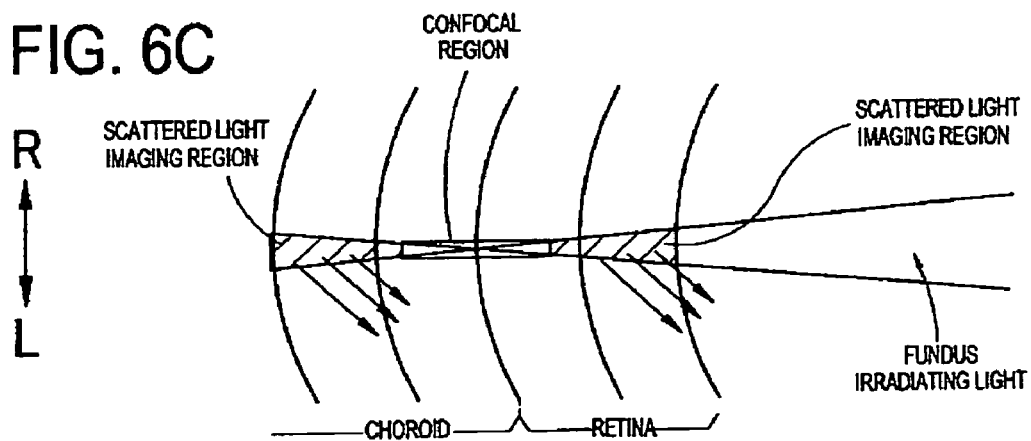

In the case where the movable member 201 is placed in the second position, the ring aperture 14 forms the passage region in the scattered light optical path K2 and the light shielding region in the confocal optical path K1, as shown in FIG. 5B. Accordingly, as shown in FIG. 6A, the light scattered in all directions (excluding the light scattered in a front direction) from front and back of the focus point of the laser beam passes through the ring-shaped opening 14b of the ring aperture 14 and enters the photo-receiving element 16, while the reflection light from the focus point of the laser beam is shielded by the black-spot plat 14a of the ring aperture 14, so that the passage of reflection light from the focus point is restricted. In other words, the ring aperture 14 is used as a ring aperture having a light shielding portion in a conjugate position with the observation plane of the fundus. In FIG. 6A to 6C, solid arrows schematically indicate traveling directions of light which will pass through the beam restriction member (the movable member 201) and enter the photo-receiving element 16.

Figure 5C:
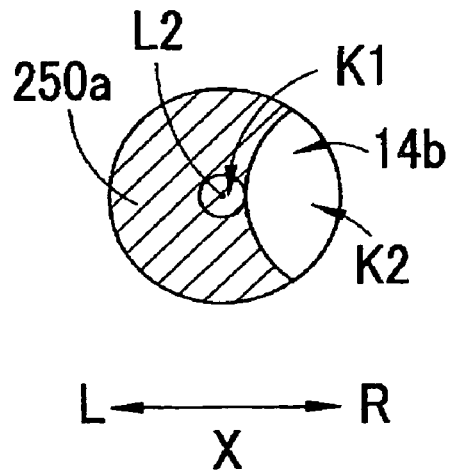

In the case where the movable member 201 is placed in the third position, furthermore, the ring-shaped opening 14b of the ring aperture 14 and the light shielding part 250a form the passage region in a right portion of the scattered light optical path K2 and the light shielding region in the confocal optical path K1 and a left portion of the scattered light optical path K2 as shown in FIG. 5C. In other words, the scattered light optical path K2 is partly shielded by the light shielding part 250a to be divided into the light shielding region and the passage region.

In this case, as shown in FIG. 6B, the reflection light from the focus point and part of the scattered light from front and back of the focus point are shielded by the light shielding part 250a. Another part of the scattered light from front and back of the focus point is allowed to pass through the passage region formed in the right portion of the scattered light optical path K2 to travel toward the photo-receiving element 16. Specifically, a part of the light shielding part 250a in the vicinity of an intersection with the optical axis L2 functions as the first light shielding part placed in a conjugate position with the focus point on the observation plane of the fundus. Furthermore, a periphery portion of the light shielding part 250a apart from the intersection with the optical axis L2 function as the second light shielding part placed in a conjugate position with the fundus. Specifically, the light shielding part 250a is used in common between the first and second light shielding part. The placement of the light shielding part

250a in the conjugate position with the fundus includes placement of the same in a nearly conjugate position with the fundus. In this case, the light shielding part 250a may be set in any position that can restrict reflection light from the focus point on the observation plane, in so far as part of the scattered light can be accurately received by the photo-receiving element 16.

Figure 7A:
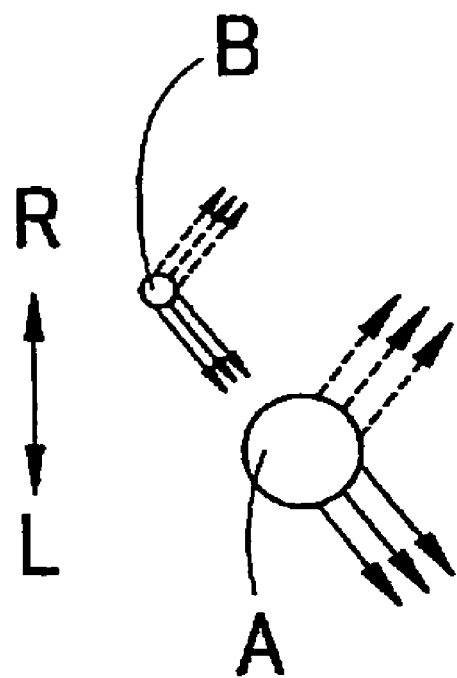
FIGS. 7A and 7B schematic diagrams to explain actions when a scattering direction of light scattered from front and back of a light condensing point is controlled.

Herein, of the light scattered from front and back of the focus point of the laser beam (the light scattered from the fundus in every direction), the light traveling from the fundus toward the right region is detected by the photo-receiving element 16. The light reflected from the focus point of the laser beam and the light traveling from the fundus toward the left region are shielded by the light shielding part 250a. Operations in this case will be explained referring to a schematic diagram of FIG. 7A. Here, it is assumed that a big material A and a small material B exist under the choroid of the examinee's eye in such a positional relation that the material B is in a deeper place than the material A and on the right side of the material A.

In the case of performing scattered light imaging with the movable member 201 being placed in the second position, the light scattered from the materials A and B in the front direction toward the apparatus is shielded by the black-spot plate 14a, while the light scattered in nearly cone shape from the materials A and B (excluding the light scattered in the front direction) reaches the photo-receiving element 16 by detouring the black-spot plate 14a. In this case, the light (solid line) scattered obliquely leftward from the material B is shielded by the material A, whereas the light (solid line) scattered obliquely leftward from the material A is received by the photo-receiving element 16. Accordingly, when comparing the light amounts detected by the photo-receiving element 16 between the laser beam scattered from the material A and the laser beam scattered from the material B, a difference in light amount will be relatively large. Accordingly, when a light receipt signal detected by the photo-receiving element 16 is imaged, the material B is obscured and only the material A appears in the created image.

On the other hand, in the case where the movable member 201 is set in the third position, the light scattered from the materials A and B in the front direction toward the apparatus is shielded by the light shielding part 250a. Of the light scattered in nearly cone shape from the materials A and B, the light (solid line) scattered from the materials A and B obliquely leftward is shielded by the light shielding part 250a. Thus, the light (broken line) scattered from the materials A and B obliquely rightward passes through the opening (the ring-shaped opening 14b) having no light shielding part 250a and then reaches the photo-receiving element 16. Consequently, when comparing the light amounts detected by the photo-receiving element 16 between the laser beam scattered from the material A and the laser beam scattered from the material B, a difference in light amount will be small. When a light receipt signal detected by the photo-receiving element 16 is imaged, accordingly, the materials A and B can be observed in the obtained image.

Figure 5D:
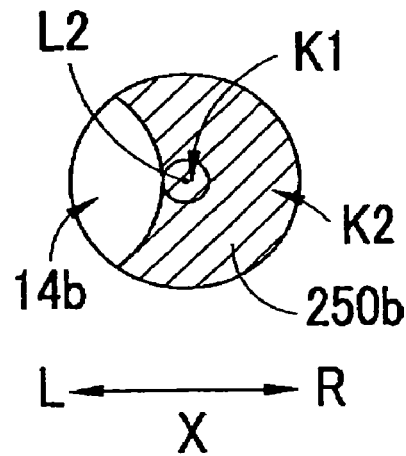

In the case where the movable member 201 is placed in the fourth position, the ring-shaped opening 14b of the ring aperture 14 and the light shielding part 250b form the passage region in the left portion of the scattered light optical path K2 and the light shielding region in the confocal optical path K1 and the right portion of the scattered light optical path K2 as shown in FIG. 5D. In other words, the scattered light optical path K2 is partly shielded by the light shielding part 250b to be divided into the light shielding region and the passage region.

In this case, as shown in FIG. 6C, the reflection light from the focus point and part of the scattered light from front and back of the focus point are shielded by the light shielding part 250b, while another part of the scattered light from front and back of the focus point is allowed to pass through the passage region formed in the left portion of the scattered light optical path K2 and travels toward the photo-receiving element 16. In other words, a portion of the light shielding part 250b near the intersection with the optical axis L2 functions as the first light shielding part placed in a conjugate position with the focus point on the observation plane of the fundus. Furthermore, a periphery portion of the light shielding part 250b apart from the intersection with the optical axis L2 function as the second light shielding part placed in a conjugate position with the fundus. Thus, the light shielding part 250b is used in common between the first and second light shielding part. The movement mechanism 200 changes the passage region of scattered light or switches the position of the passage region of scattered light.

Herein, of the light scattered from front and back of the focus point of the laser beam (the scattered light from the fundus in every direction), the light traveling from the fundus toward the left region is detected by the photo-receiving element 16. Furthermore, the light reflected from the focus point of the laser beam and the light traveling from the fundus toward the right region are shielded by the light shielding part 250b.

Figure 7B:
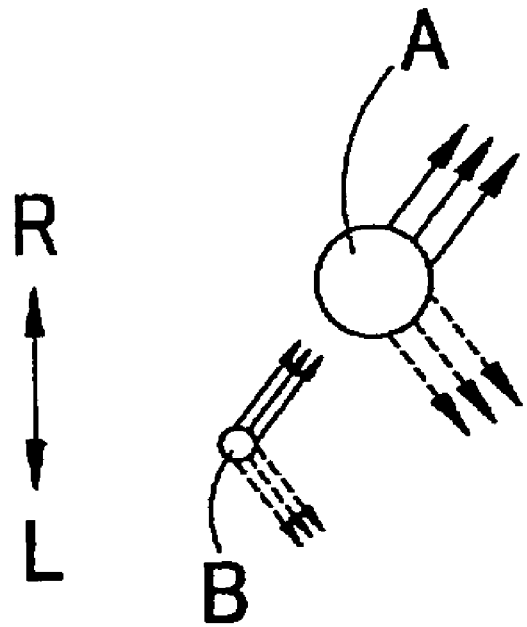

The following explanation will be given to operations in the case where the movable member 201 is placed in the fourth position, referring to FIG. 7B. Here, it is assumed that a big material A and a small material B exist under the choroid of the examinee's eye in such a positional relation that the material B is in a deeper place than the material A and on the left side of the material A.

When the movable member 201 is set in the fourth position, the light scattered from the materials A and B in the front direction toward the apparatus is shielded by the light shielding part 250b. Of the light scattered in nearly cone shape from the materials A and B, the light (solid line) scattered from the materials A and B obliquely rightward is shielded by the light shielding part 250b. On the other hand, the light (broken line) scattered from the materials A and B obliquely leftward is allowed to pass through the opening (the ring-shaped opening 14b) having no light shielding part 250b and then reaches the photo-receiving element 16. Consequently, when comparing the light amounts detected by the photo-receiving element 16 between the laser beam scattered from the material A and the laser beam scattered from the material B, a difference in light amount will be small. When a light receipt signal detected by the photo-receiving element 16 is imaged, accordingly, the materials A and B can be observed in the obtained image.

In the case of performing the scattered light imaging in which the light scattered from front and back of the focus point of the laser beam irradiated to the fundus is detected by the photo-receiving element 16 and imaged, the above configuration makes it possible to control a scattering direction (a scattering angle) of the scattered light to be received by the photo-receiving element 16.

Accordingly, it is possible to image fine biological materials which would be difficult to be imaged by scattered light imaging using a conventional ring aperture 14. A useful image in diagnosis of fundus diseases can therefore be obtained.

To efficiently control the direction of the scattered light to be received by the photo-receiving element 16, it is preferable to shield a half or more portion of the ring-shaped scattered light optical path, as explained above. In order to allow the photo-receiving element 16 to receive components of the scattered light in only a predetermined direction and restrict the reflection light from the focus point on the fundus observation plane, it is more preferable to form a light shielding region in the confocal optical path and form a passage region having a center angle of 120° or less about the imaging optical axis L2 in the scattered light optical path while forming a light shielding region in another portion of the scattered light optical path, as shown in FIGS. 5C and 5D. Furthermore, it is more preferable to form a light shielding region in the confocal optical path and form a passage region having a center angle of 90° or less about the imaging optical axis L2 in the scattered light optical path while forming a light shielding region in another portion of the scattered light optical path.

In the above explanation, part of the movable member 201 on which the variable diaphragm 13 and the ring aperture 14 are mounted is used as the light shielding part 250a or the light shielding part 250b, and the movable member 201 is moved by the movement mechanism 200 to change the passage region of scattered light. The invention, however, is not limited to such configuration. Specifically, the beam restriction member placed in the conjugate position with the fundus and used in common between the first and second light shielding parts has only to have a light shielding part for restricting the reflection light from the focus point and restricting the passage region of scattered light and an opening of a predetermined size allowing part of the scattered light from front and back of the focus point to pass therethrough toward the photo-receiving element 16. The beam restriction member also has only to have the movement mechanism for moving the beam restriction member on a plane orthogonally intersecting with the imaging optical axis L2 in order to change the passage region of scattered light which will pass through the opening. Furthermore, the movement mechanism may be arranged to selectively move the opening to several positions to change the passage region of reflection light which will pass through the opening. In this case, the movement mechanism is controlled by the controller 20 to switch the position of the opening. For instance, it is conceivable to provide a light shielding member having a circular opening of a predetermined diameter (e.g., an equal size to the outer periphery of the ring-shaped opening 14b) placed in the conjugate position with the fundus, and control the movement mechanism by the controller 20 to place the light shielding member in such a position as to restrict the reflection light from the focus point and restrict the passage region of scattered light. In this case, the light shielding member having the circular opening has only to be moved among several positions to change the passage region of scattered light. It should be noted that the light shielding member may be arranged to be movable in not only one-dimensional direction but also two-dimensional direction.

The light shielding member having the opening of a predetermined size and the movement mechanism for moving the light shielding member on a plane orthogonally intersecting with the imaging optical axis L2 may also be configured as shown in FIG. 8.

The movable member 201 shown in FIG. 8 includes, besides the variable diaphragm 13 and the ring aperture 14, a plurality of light shielding members 300 to 303 each serving as the light shielding part arranged on the movable member 201 and having an opening for allowing part of scattered light to pass therethrough toward the photo-receiving element 16. In this case, the light shielding members 300 to 303 are different in opening position to provide different passage regions and light shielding regions for restricting part of the scattered light from front and back of the focus point. To be more concrete, respective openings OP and light shielding parts SH are different in position. Herein, the movable member 201 is moved by activation of the drive part 210 to dispose either one of central portions 300c to 303c of the light shielding members 300 to 303 onto the optical axis L2. Thus, a selected one of the light shielding members 300 to 303 is changeably placed in the optical path of the imaging optical system.

In the case where the central portion 300c of the light shielding member 300 is placed on the optical axis L2, the passage region is formed in an upper portion, in the drawing sheet, of the scattered light optical path K2 shown in FIGS. 4 and 5A to 5D and the light shielding region is formed in the confocal optical path K1 and a lower portion of the scattered light optical path K2 in the drawing sheet. When the central portion 301c of the light shielding member 301 is placed on the optical axis L2, the passage region is formed in a lower portion of the scattered light optical path K2 in the drawing sheet and the light shielding region is formed in the confocal optical path K1 and an upper portion of the scattered light optical path K2 in the drawing sheet. Furthermore, when the central portion 302c of the light shielding member 302 is placed on the optical axis L2, the passage region is formed in a right portion of the scattered light optical path K2 in the drawing sheet and the light shielding region is formed in the confocal optical path K1 and a left portion of the scattered light optical path K2 in the drawing sheet. When the central portion 303c of the light shielding member 303 is placed on the optical axis L2, the passage region is formed in a left portion of the scattered light optical path K2 and the light shielding region is formed in the confocal optical path K1 and a left portion of the scattered light optical path K2.

As above, the use of the light shielding members different in position of light shielding region in the scattered light optical path enables selection of a direction for restricting scattered light from many directions, thereby increasing the possibility of finding fine biological materials. Each of the aforementioned light shielding members 300 to 303 is formed to divide the scattered light optical path K2 into about half as the passage region and the light shielding region. As an alternative, it may be configured to divide the optical path K2 into about three-fourth part as the light shielding region and about one-fourth part as the passage region.

For selectively placing the light shielding members 300 to 303 having the openings different in position, it may be arranged to provide various light shielding members on a rotary plate rotatable about a rotation axis parallel to the imaging optical axis L2, and rotate the rotary plate to selectively dispose one of the light shielding members into the optical path of the imaging optical system. As an alternative, a liquid crystal shutter for electrically controlling transmission and shielding of light may be provided in a conjugate position with a fundus to change between the passage region and the light shielding region.

In the above explanation, a predetermined light shielding member is used in common between the first and second light shielding parts. Alternatively, it may be arranged to include a first light shielding member having a light shielding part in a conjugate position with the focus point on the observation plane of the fundus and a second light shielding member placed in front or back of the first light shielding member to restrict part of scattered light.

To be specific, a configuration shown in FIG. 9 is conceivable, in which the ring aperture 14 is placed as the first light shielding member in a conjugate position with the fundus in the optical path of the imaging optical system so that the black-spot 14a (the light shielding part) is located in a conjugate position with the focus point on the observation plane of the fundus, and a light shielding member 400 is placed as the second light shielding member in front of (on the lens 12 side) and near the ring aperture 14 to restrict part of the scattered light having passed through the ring-shaped opening 14b of the ring aperture 14 toward the photo-receiving element 16. In FIG. 9, components assigned with the same reference signs as those in FIG. 2 are identical or similar in configuration to those in FIG. 2. A movement mechanism 401 is arranged to move the light shielding member 400 in order to change the passage region of the scattered light which passes through the ring-shaped opening 14b of the ring aperture 14. The movement mechanism 401 is adapted to move the light shielding member 400 to one of several positions. The controller 20 controls the movement mechanism 401 to switch the position of the light shielding member 400.

Concretely speaking, the movement mechanism 401 for moving the light shielding member 400 on a plane (in right and left direction) orthogonally intersecting with the imaging optical axis L2 of the imaging optical system includes a drive part 410 (e.g. a pulse motor) serving as a drive source to move the light shielding member 400, a screw rod 411 connected to a rotation shaft of the drive part 410, and a connection member 405 formed with a female screw part which engages with a male screw part of the screw rod 411 and connected to the movable member 401. In this case, the position of the light shielding member 400 is changed from right to left or reverse by activation of the drive part 410.

The placement of the ring aperture 14 in a conjugate position with the fundus and the placement of the black spot 14a in a conjugate position with the focus point on the observation plane of the fundus each include placement in a nearly conjugate position. In this case, the ring aperture 14 and the black spot plate 14a may be placed in any position that can restrict reflection light from the focus point on the observation plane, in so far as part of scattered light can be accurately received by the photo-receiving element 16. The farther from the conjugate position, the larger the beam diameter of the reflection light from the focus point on the observation plane of the fundus is. Accordingly, a larger black spot plate 14a is required for such a large beam diameter. Furthermore, shielding of scattered light by the black spot plate 14a will decrease an amount of scattered light to be received by the photo-receiving element 16. It is therefore necessary to design optical placement in a permissible range.

It is to be noted that in FIG. 9 the light shielding member 400 may be placed in back of and close to the ring aperture 14. Although the light shielding member 400 in FIG. 9 is configured to move along the plane orthogonally intersecting with the optical axis L2, the light shielding member 400 has only to be placed in a position that can restrict the passage region of scattered light in the ring-shaped opening 14b of the ring aperture 14. For instance, an additional system may be provided to move the light shielding member 400 linearly on the plane orthogonally intersecting with the optical axis L2.

Figure 10:
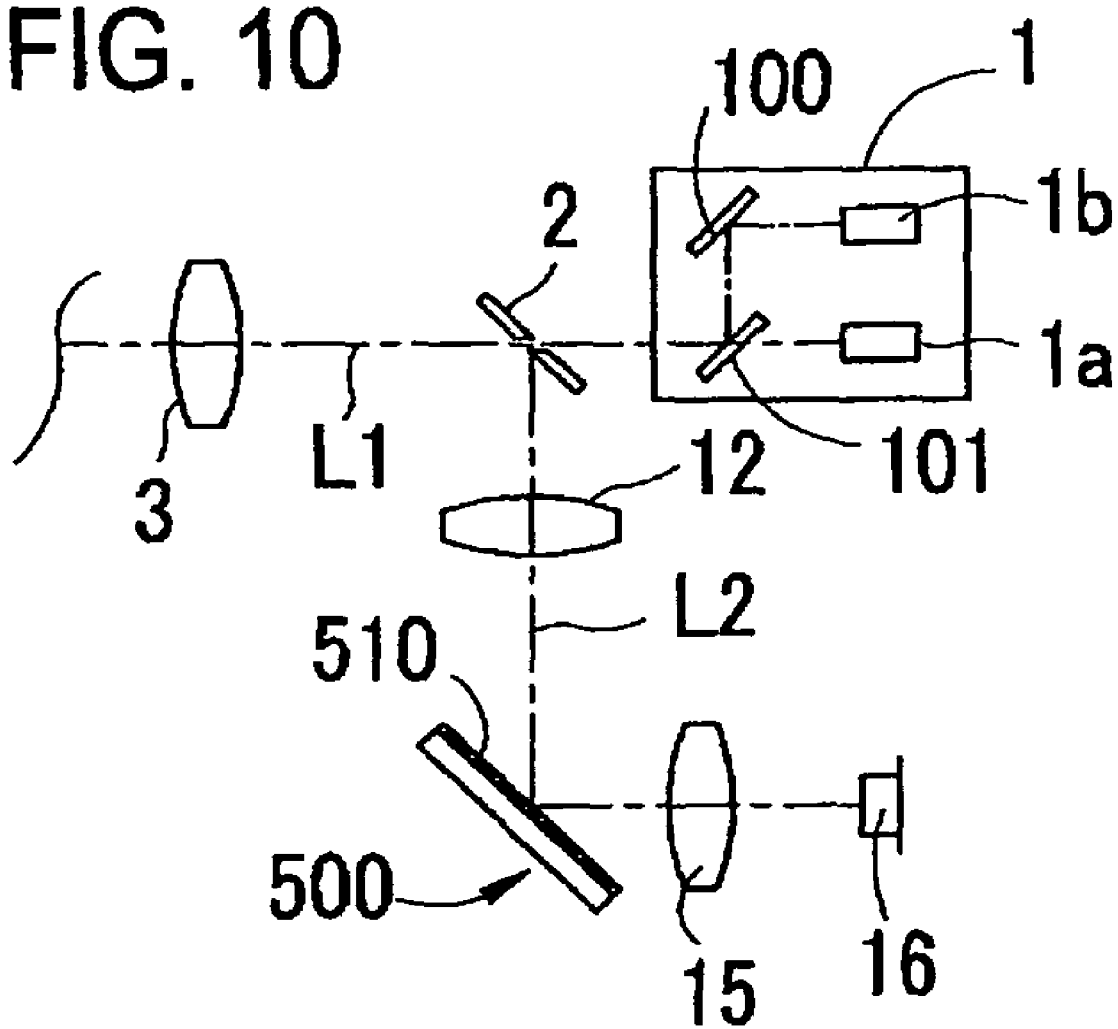
FIG. 10 is a view showing a case where a micro mirror device is used as a beam restriction member.

In the above explanation, it is arranged to control passage and shielding of reflection light from the focus point on the fundus and scattered light from front and back of the focus point by use of the light shielding member(s) having a property of absorbing light. Any other configuration may be adopted if only it can restrict light which travels toward the photo-receiving element 16 along the optical path of the imaging optical system. For instance, a micro mirror device 500 including fine mirrors 510 placed in two dimensions may be provided in a conjugate position with the fundus (see FIG. 10). In this case, a traveling direction of reflection light to be changed by each mirror 510 is controlled to restrict (shield) the reflection light of the laser beam that will travel toward the photo-receiving element 16. Accordingly, part of the scattered light having passed through the micro mirror device 500 is received by the photo-receiving element 16. In the above configuration, the lens 15 and the photo-receiving element 16 are arranged in a reflecting direction (destination) of the light reflected by the micro mirror device 500 so that the reflection light is received by the photo-receiving element 16.

In the above configuration, it may be arranged to switch the passage region of scattered light to image two images by scattered light passing through the passage regions symmetric with respect to the imaging optical axis L2, and to use the two imaged images as a pair of stereoscopic observation images. Specifically, switching is made between a first passage region formed by changing the passage region and a second passage region formed by changing the passage region to be symmetric with the first passage region with respect to the imaging optical axis L2. Then, a first scattered light image obtained when the passage region is set as the first passage region and a second scattered light image obtained when the passage region is set as the second passage region are acquired as a pair of stereoscopic observation images.

More specifically, when the movable member 201 (see FIG. 2) is moved to either the third position or the fourth position mentioned above, the passage region of scattered light is changed symmetrically with respect to the optical axis L2 (see FIGS. 5C and 5D). In this case, the memory 25 has stored in advance the third position (first formation information) of the movable member 201 set to form the first passage region (e.g., the passage region shown in FIG. 5C) and the fourth position (second formation information) of the movable member 201 set to form a second passage region (e.g., the passage region shown in FIG. 5D). Accordingly, the controller 20 drives and controls the drive part 210 based on the third position and the fourth position stored in the memory 25.

When the scattered light imaging is performed in each of the third and fourth positions, two (a pair of) scattered light images are imaged by the scattered light passing through the passage regions symmetric with each other with respect to the optical axis L2. At that time, the controller 20 causes the memory 25 to store the pair of imaged scattered light images as the stereoscopic observation images. In this case, the controller 20 causes the memory 25 to store scattering directions of the scattered light received by the photo-receiving element 16 on the fundus (e.g. a right direction and a left direction) in association with imaged scattered light images. It is to be noted that switching of the symmetric passage regions may be performed by electric control by a predetermined changeover switch or conducted manually.

The pair of imaged scattered light images stored in the memory 25 include the same imaging portion but they are made by the light scattered from the fundus in different directions and received by the photo-received element 16. Commonly, two fundus images different in parallax are used for stereoscopic imaging using a fundus camera. In this embodiment, however, two fundus images (imaged scattered light images) are obtained by scattered light different in scattering direction and hence they can appear as if they had parallax.

The pair of imaged images obtained in the above technique can be used for stereoscopic observation in various manners. For instance, a pair of imaged images is displayed in a stereoscopic view on a predetermined image display part (e.g. the monitor 24). An observer (an examiner) who sees the image display part is allowed to view the scattered light image stereoscopically by his/her binocular parallax. To be more specific, the pair of imaged images is displayed side by side on the image display part and the observer peers through a special stereo viewer to observe the images stereoscopically (a display capable of stereoscopically displaying an image may be adopted without using the special stereo viewer). In the case where the pair of right and left imaged images is displayed side by side, a first scattered light image (a scattering direction: rightward) obtained from the light that travels rightward from the fundus is displayed on the right section in a screen of the image display part and a second scattered light image (a scattering direction: leftward) obtained from the light that travels leftward from the fundus is displayed on the left section in the screen of the image display part may be displayed based on the scattering direction information and each imaged image which are stored in the memory 25. It is to be noted that the pair of imaged images may be printed and placed side by side in a special stereo viewer for allowing stereoscopic observation.

As described above, by the stereoscopic observation using the pair of scattered light images obtained in the above manner, it is possible to stereoscopically observe a positional relation of the choroid, an affected part, retinal vessels, and others of the examinee's eye, thereby adding information in a depth direction, and thus obtain a useful image in diagnosis of fundus diseases.

In the above explanation, two scattered light images are imaged by scattered light passing through the symmetric passage regions. The passage regions of scattered light have only to be symmetric with respect to the imaging optical axis L2. For example, a pair of stereoscopic observation images may be acquired from two scattered light images of scattered light passing through the passage regions vertically symmetric with respect to the imaging optical axis L2. In the case where the pair of upper and lower imaged images are arranged laterally side by side for stereoscopic view, two scattered light imaged images, that is, a scattered light image obtained by the light traveling upward from the fundus and a scattered light image obtained by the light traveling downward from the fundus, are turned in the same direction by 90° respectively to be placed laterally side by side, and then stereoscopic observation is performed.

The above explanation shows a technique of stereoscopically viewing a scattered light image by use of binocular parallax of an observer (an examiner). An alternative is to apply stereo matching process to a pair of scattered light image data acquired as above to obtain three-dimensional data of the fundus. A three-dimensional stereoscopic image may also be displayed by image processing based on the obtained three-dimensional data. About the stereo matching process, refer to for example JP2000-126134A (U.S. Pat. No. 6,224,212). Another alternative is to construct a three-dimensional stereoscopic image based on three or more scattered light images different in scattering direction from the fundus.

In the above explanation, the passage region of scattered light is changed by movement of the beam restriction member provided in a predetermined place of the imaging optical system. Alternatively, the reflection light and the scattered light from the fundus have only to be moved with respect to the beam restriction member when passing through the fundus conjugate plane formed in the imaging optical system. For instance, it may be arranged such that the beam restriction member of the imaging optical system is fixed and any one of other optical members of the imaging optical system is moved with respect to the beam restriction member. For example, in the optical system shown in FIG. 1, conceivably, the perforated mirror 2 is rotated or turned right and left about the center of the opening of the perforated mirror 2 placed in conjugate relation with the photo-receiving element 16, from the state (see FIG. 5B) where the reflection light from the focus point on the observation plane concentrates on the center of the ring aperture 14. Accordingly, the above state will be changed to the state where the reflection light from the focus point on the observation plane concentrates on the light shielding part 250a (see FIG. 5C) or the state where the reflection light from the focus point on the observation plane concentrates on the light shielding part 250b (see FIG. 5D), thereby changing the passage region of scattered light. In this case, the perforated mirror 2, lens 12, lens 15, and photo-receiving element 16 may be simultaneously rotated right and left about the center of the opening of the perforated mirror 2.

In the case of changing the passage region of scattered light as above, the size of the passage region may be changed optionally by operation of a predetermined switch. In this case, for example, the controller 20 moves the movable member 201 shown in FIGS. 1 and 2 from the third position to the right according to an operation signal from the switch. In this state, a central angle of the passage region centered on the imaging optical axis L2 is changed and the light shielding region formed adjacent to the passage region relative to the confocal optical path (the imaging optical axis L2) is changed to become wider toward the periphery (in a direction farther from the optical axis L2). Movement of the movable member 201 from the fourth position to the left allows the same change. It should be noted that the invention is not limited to the above configuration and may be arranged such that the central angle of the passage region and the size of the light shielding region formed adjacent to the passage region relative to the confocal optical path (the imaging optical axis L2) may be changed separately. In this case, for example, a crystal liquid shutter for electrically controlling transmission and shielding of light is conceivably used.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A fundus imaging apparatus comprising:
   an irradiation optical system comprising a light source which emits a laser beam and a scanner which two-dimensionally scans the laser beam on a fundus of an examinee's eye, the irradiation optical system being adapted to focus the laser beam emitted from the light source on the fundus to form a confocal region in a direction of an optical axis of the irradiation optical system;
   an imaging optical system comprising a photo-receiving element which receives reflection light of the laser beam reflected from the fundus, the imaging optical system being adapted to focus the reflection light from the fundus and receive the reflection light by the photo-receiving element;
   a beam restriction member placed in an optical path of the imaging optical system, the beam restriction member comprising:
   one of an opening through which part of the reflection light from the fundus outside the confocal region in front and back of the confocal region in the optical axis direction is allowed to pass toward the photo-receiving element and a mirror part which reflects the part of the reflection light from the fundus outside the confocal region in the front and back of the confocal region toward the photo-receiving element; and
   a light shielding part which shields the reflection light from the fundus in the confocal region and the part of the reflection light from the fundus outside the confocal region in the front and back of the confocal region;

wherein the light shielding part includes a first light shielding part placed in a conjugate position with a focus point of the laser beam on the fundus and a second light shielding part placed in a nearly conjugate position with the fundus and adapted to shield part of an optical path of the reflection light, the optical path of the refection light is formed around the first light shielding part; and a drive part which changes a light shielding region to be provided by the second light shielding part while shielding the reflection light from the fundus in the confocal region by the first light shielding part.

2. The fundus imaging apparatus according to claim 1, wherein the opening of the beam restriction member has a predetermined size, and the beam restriction member further comprises a movement mechanism for moving the beam restriction member on a plane orthogonally intersecting with the optical axis of the imaging optical system to change a passage region of the reflection light in the opening.

3. The fundus imaging apparatus according to claim 1 further comprising:

a control unit being adapted to control activation of the drive part to switch a passage region of the reflection light in the opening between a first passage region and a second passage region symmetric with the first passage region with respect to the optical axis of the imaging optical system.

4. The fundus imaging apparatus according to claim 1, wherein the beam restriction member is a micro mirror device placed in a conjugate position with the fundus.

5. The fundus imaging apparatus according to claim 1, wherein the second light shielding part is arranged to shield half or more portion of the reflection light optical path formed around the first light shielding part.

6. The fundus imaging apparatus according to claim 3, further comprising:

an image acquiring part being adapted to obtain a fundus image based on a light receipt signal outputted from the photo-receiving element and obtain, as a pair of stereoscopic observation images, a first image acquired when the reflection light is received by the photo-receiving element through the first passage region and a second image acquired when the reflection light is received by the photo-receiving element through the second passage region.

7. A fundus imaging apparatus comprising:

an irradiation optical system including a light source which emits a laser beam and a scanner which two-dimensionally scans the laser beam on a fundus of an examinee's eye, the irradiation optical system being adapted to form the laser beam emitted from the light source on the fundus; and an imaging optical system including:

a photo-receiving element which receives reflection light of the laser beam reflected from the fundus;

a first diaphragm placed in a nearly conjugate position with the fundus, the first diaphragm having a first opening placed on an optical axis to pass part of the reflection light traveling from a nearly conjugate plane to the photo-receiving element, the part of the reflection light traveling near the optical axis, the first diaphragm being configured to shield another part of the reflection light traveling the nearly conjugate plane to the photo-receiving element, a second diaphragm placed in the nearly conjugate position with the fundus, the second diaphragm having a second opening placed in a position out of the optical axis to pass part of the reflection light traveling from the nearly conjugate plane to the photo-receiving element, the part of the reflection light traveling from a predetermined direction in a region apart from the optical axis, the second diaphragm being configured to shield other part of the reflection light traveling from the nearly conjugate plane to the photo-receiving element; and a switch unit which selects the diaphragm to be placed in an optical path from between the first diaphragm and the second diaphragm;

the imaging optical system being configured to focus the reflection light from the fundus and receive the reflection light passing through one of the first diaphragm and the second diaphragm by the photo-receiving element.

8. The fundus imaging apparatus according to claim 7, wherein the imaging optical system includes a third diaphragm placed in the nearly conjugate position with the fundus, the third diaphragm having a third opening to pass light from all directions in the region apart from the optical axis, a part of the third opening being also used as the second opening, and the switch unit selects the diaphragm to be placed on the optical path from among the first diaphragm, the second diaphragm, and the third diaphragm.

9. The fundus imaging apparatus according to claim 7, wherein the imaging optical system includes a third diaphragm placed in the nearly conjugate position with the fundus, the third diaphragm having a third opening to pass light from all directions in the region apart from the optical axis, the third diaphragm is a separate member from the second diaphragm, and the switch unit selects the diaphragm to be placed on the optical path from among the first diaphragm, the second diaphragm, and the third diaphragm.

10. The fundus imaging apparatus according to claim 7, wherein the switch unit is a liquid crystal shutter placed in the nearly conjugate position with the fundus and configured to electrically control transmission and shielding of light, the liquid crystal shutter being formed with the first diaphragm and the second diaphragm.

11. The fundus imaging apparatus according to claim 7, wherein the imaging optical system includes a plurality of second diaphragms with second openings in different positions in the region apart from the optical axis.

12. The fundus imaging apparatus according to claim 7, wherein the imaging optical system includes a plurality of second diaphragms with second openings in different positions symmetrical with respect to the optical axis in the region apart from the optical axis.

* * * * *